United States Patent [19]

Brown et al.

[11] Patent Number: 5,496,308
[45] Date of Patent: *Mar. 5, 1996

[54] RADIAL LASER DELIVERY DEVICE

[76] Inventors: Joseph Brown, 1706 Brookgreen Way, Acworth, Ga. 30101; Wolfgang Neuberger, KamphausenerWeg 19, 4050 Monchengladbach 3, Germany

[ * ] Notice: The term of this patent shall not extend beyond the expiration dat of Pat. No. 5,292,320.

[21] Appl. No.: 173,891

[22] Filed: Dec. 27, 1993

Related U.S. Application Data

[63] Continuation-in-part of Ser. No. 908,382, Jul. 6, 1992, Pat. No. 5,292,320.

[51] Int. Cl.$^6$ ................................................ A61M 29/02
[52] U.S. Cl. ........................... 606/15; 606/17; 606/14
[58] Field of Search .................... 606/7, 10–16; 607/89

[56] References Cited

U.S. PATENT DOCUMENTS 4,740,047  4/1988  Abe et al. .
5,019,079  5/1991  Spears et al. .
5,057,099  10/1991 Rink .
5,292,320  3/1994  Brown et al. ............................ 606/14

*Primary Examiner*—Stephen C. Pellegrino
*Assistant Examiner*—Michael Peffley

[57] ABSTRACT

The present invention involves a medical delivery system capable of emitting radiation with wavelengths between 190 nm and 16 um in one or more essentially directed, predetermined patterns. It includes at least one solid optical fiber, having a core and a cladding on the core. The cladding has a refractive index smaller than the core, having an input end suitably configured to connect to an appropriate radiation source and having a distal end in the proximity of which two or more grooves are penetrating into the core. The grooves have at least partial reflector capability so as to deflect radiation thereto radially in one or more predetermined patterns. The invention also includes methods of performing medical procedures utilizing the aforesaid device.

22 Claims, 6 Drawing Sheets

RADIAL LASER DELIVERY DEVICE

REFERENCE TO RELATED CASE

This application is a continuation-in-part of application Ser. No. 07/908,382 filed Jul. 6, 1992 now U.S. Pat. No. 5,292,320.

BACKGROUND OF THE INVENTION

1. Field of the Invention

This invention relates to a laser delivery device, and more particularly to such delivery devices that a emit radially well directed emission pattern from the distal end of an optical fiber.

2. Prior Art Statement

Technological change in laser delivery devices is rapidly taking place in the laser medical field with the onset of minimally invasive procedures such as laser laparoscopy. The laparoscopist, a physician or surgeon who performs laparascopies, is often challenged with positioning the delivery device, i.e., the optical fiber(s), at angles radially to the laparoscope axis in order to irradiate the target perpendicularly. However, in many cases moving a laparoscope radially is very difficult or is impossible. As an alternative, the laparoscope, which is normally rigid, may have an adjustable fiber deflector called a bridge. The bridge may be adjusted at the proximal end causing radial movements to the distal end of the fibers. This adjustment is, however, limited by the bend radius of the fibers and/or the bridge device and cannot offer full capabilities. Therefore, techniques to emit radiation radially from the distal end of the fiber without bending are needed.

Reflecting tips secured on the distal fiber end, such as metal caps incorporating a mirror surface at a 45° angle relative to the fiber axis are state of the art and have been used successfully in procedures such as lithotripsy with high pulse powered (Q-switched) Yttrium Aluminum Garnet Lasers.

For many surgical procedures requiring an even illumination (such as prostate treatment or photodynamic therapy) the point source-like radiation pattern from this known device is ill suited.

The state of the art devices used in photodynamic therapy incorporate a glue, i.e. epoxy, containing cap with scattering medium dispersed in it. These caps can produce a relatively homogeneous radial pattern. However, the output is diffuse and they are somewhat limited in power handling capability due to the limitations of the glue.

U.S. Pat. No. 5,019,075 to Spears et al describes a device for transluminal angioplasty of a stenosed artery with a diffusing area along an optical fiber created by removing the cladding and abrading the fiber core surface such that the fiber core surface is roughened. Diffuse radiation thus exits from the fiber circumference in random directions resulting in radiation energy being applied to the entire circumference of a selected region of an artery simultaneously. Although a given ray may indeed be reflected in a direction opposite to the roughened surface part, its direction will be as ambiguous as the roughened corner it is reflected on. The scattering media described by Spears would also create diffuse instead of well directed radiation patterns. This is unlike the present invention wherein a distinctly different, more controlled radiation pattern is emitted, specifically radially well directed (non diffuse) emission from an extended section of the fiber achieved by grooves having been formed in a predetermined pattern rather than mere roughening of the core surface.

In summary, the present state of the art for radial laser radiation delivery is restricted to either point sources (size of the source comparable to the fiber cross section) or to essentially diffuse radiators with limited power handling capabilities. U.S. Pat. No. 4,740,047 describes a point source type of device using a cut fiber with a reflective surface to deflect a beam for lateral application.

While methods to control the fiber tip temperature aimed at preventing damage to the distal tip of the laser delivery device have been described in U.S. Pat. No. 5,057,099 no control method has been described to prevent or limit damage to the tissue itself that seems applicable to treatments such as laser prostatectomy. Thus, while this recently issued patent allows for temperature control to optimize particular surgical or medical procedures, it does not address or satisfactorily resolve the need for proper lateral and radial delivery of laser beams to satisfy varied needs for varied procedures.

Thus, the prior art neither teaches nor renders obvious the present invention device set forth herein.

SUMMARY OF THE INVENTION

Described is a device capable of delivering high laser power at selected angles or any angle essentially radially to the axis of an optical fiber. The fiber emits the laser radiation from a wider area at the distal end in a well directed, essentially non-diffuse pattern with a plurality of predetermined reflective surfaces, having different angles or sizes, within the fiber itself.

Surgical procedures, such as transurethral laser prostatectomy, are beneficially performed using preferred embodiments of the device. The device may comprise feedback control mechanisms from the tissue to regulate radiation delivery dosimetry with procedural requirements.

BRIEF DESCRIPTION OF THE DRAWINGS

The invention, together with further objects, advantages, aspects and features thereof, will be more clearly understood from the following description taken in connection with the accompanying drawings.

DESCRIPTION OF THE PREFERRED EMBODIMENTS

It is an object of this invention to provide a new and improved radial laser delivery device to overcome the disadvantages of prior radial laser delivery devices, such as power handling capability, area of coverage, extent of coverage, radially directedness of radiation from an extended source, etc. By "radial" and "radially" are meant extending outwardly from the central axis of a fiber and not parallel thereto. In this application, they are meant to include extending outwardly at right angles as well as at any other angles and to include full circumference and only partial circumference radiation.

Another object of this invention is to describe a control mechanism and an improved device method to carry out treatments such as laser prostatectomy and photodynamic therapy.

Figure 1:
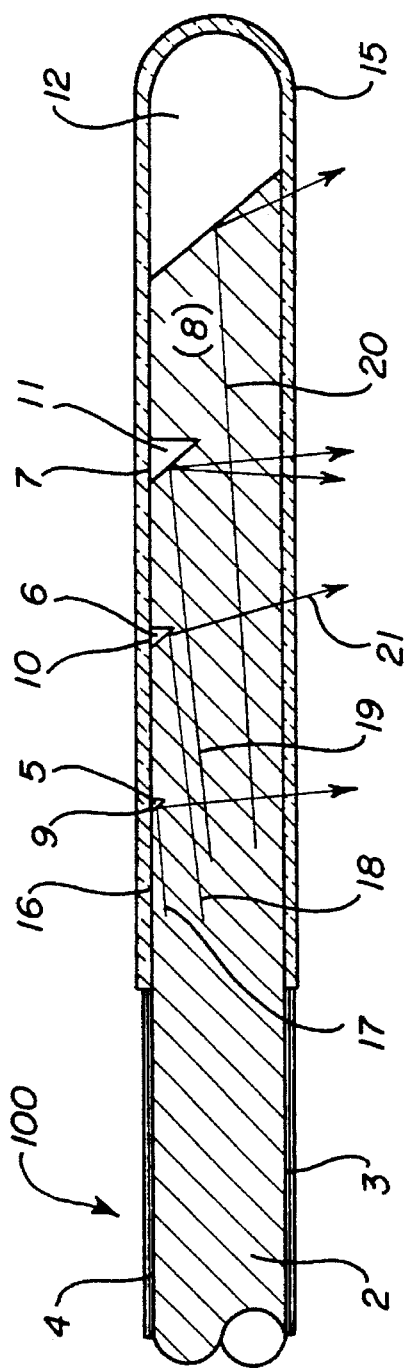
FIG. 1 is a side view of a radial medical radiation delivery device using gas pockets created by the core and a transparent cap for total reflection.

FIG. 1 illustrates a side view of present invention device 100, a typical preferred embodiment of the invention, at its distal end. The optical fiber 1 has a core 2, a cladding 3 and one or more protective coating layers 4. Core 2 is grooved on one side, and grooves 5, 6 and 7 are of increasing size and/or angles, as shown. Core 2 distal end 8 is encapsulated with optional protective, transparent cap 15 over a predetermined length so as to cover all the grooves 5, 6 and 7; this resulting in a series of gas pockets 9, 10, 11 and 12. The gas pockets may typically contain clean air or an inert gas such as nitrogen or argon. The cap can be affixed to the fiber by any medically safe glue 16. The gas atmosphere under which the cap placement and fixation takes place will be the type of gas enclosed when the cap is sealed to the fiber using a leaktight glue. If the inclination of the fronts of the grooves (facing incoming radiation) measured from the most inclined ray 17, 18 and 19 travelling in the fiber 1 is chosen such that it is lower than the angle of the total reflection limit between the optical fiber core and air, all rays coming through the fiber from the proximal end (input end of the radiation source, or laser) will be totally reflected and thus exit in radial direction as shown by the typical arrows such as arrow 21.

By progressively increasing the depth of each groove towards the distal end 8 of the fiber 1, more and more radiation is diverted from the axial path into the radial direction resulting in the desired extended directed radiation. This creates a defined, predetermined area of radiation application that is much greater than a reflected point source.

One type of fiber well suited to practice the present invention may be a plastic clad fiber where the optical cladding consists of a polymer (plastic) having a refractive index lower than the core. In the case where quartz glass is used as a core material the plastic cladding may be typically either a silicon (for instance RTV 615 from General Electric Company or a flourinated acrylate (such fibers can be obtained under the trade name Hard Clad Silica Fibers from Ensign Bickford or 3M). Another suitable type of fiber may be a glass/glass type fiber where the optical cladding consists of material essentially similar to the core. In the case where quartz glass is used the core could typically be a pure fused fused silica while the quartz glass cladding contains fluorine as a dopand so as to lower the refractive index of the cladding material relative to the core. Alternatively, the core could contain a germanium dopand in order to increase its refractive index and in this case the cladding may be, for example, pure silica. Typically, glass/glass fibers are coated by one or two additional polymer layers to protect the delicate glass surface.

The present invention will work in principle with the cladding on as well as with the cladding removed. Whether to preferably remove or not remove the cladding is illustrated by the following examples:

In the case of a quartz/quartz fiber it would be rather impractical to remove the quartz glass cladding, although in principle it can be done, for instance by etching the fiber tip with suitable acid for a defined time and afterwards polishing the surface, for instance, with a $CO_2$ laser.

In the case of a silicone clad quartz/quartz fiber, it is difficult to bond a cap, if desired, to silicone and since the silicone tends to cause problems when grinding the grooves, it is preferably removed. The invention will work nevertheless if either an air gap is maintained between the glass fiber tip and the protective capillary or the capillary itself is chosen to have a lower refractive index than the fiber core, for instance by being manufactured out of fluorine doped quartz. The glue used to affix the capillary on the fiber should have a lower refractive index than the fiber core as well. Suitable glues are sold by epoxy Technologies, Inc. (Epotec 394), for instance.

Figure 2:
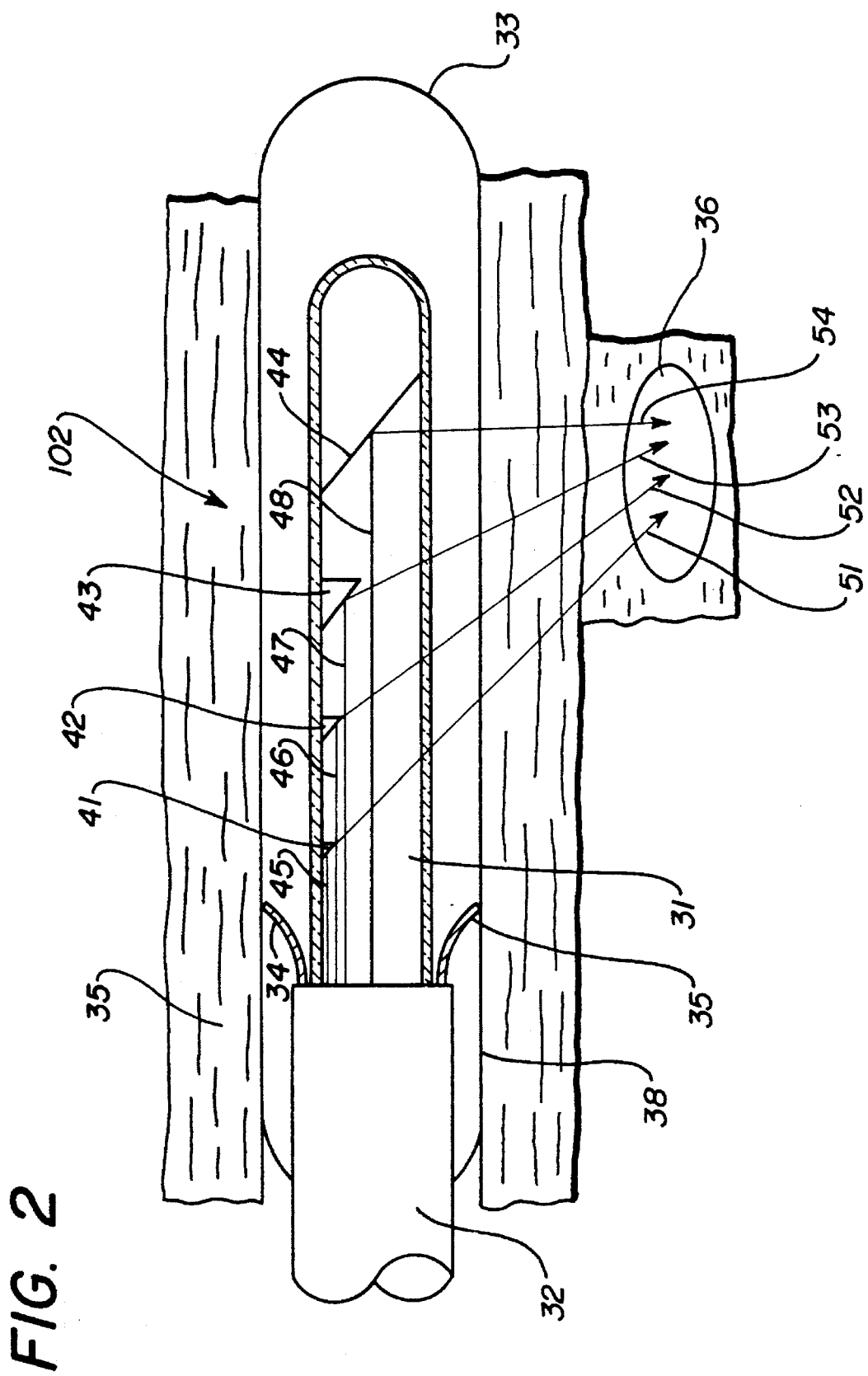
FIG. 2 shows another radial medical radiation delivery device that can be freely positioned inside a transparent, inflatable balloon incorporating temperature sensing fibers as well, placed to irradiate the prostate.

FIG. 2 now illustrates how another such device 102 is employed to shrink the prostate gland and thus provide a free passage in the urethra. As known, the prostate gland can swell and thus result in an inconvenience for a high number of men, particularly at higher age, in as much as the urethra is thus partially blocked and the free flow of urine can be obstructed. It is known that by irradiating the prostate, and thus degenerating and shrinking it this inconvenience can be removed, and a free passage restored. Surgical procedures for degenerating and shrinking the prostate in which a cystoscope and fiber optic are employed are familiar to those skilled in the art. Photodynamic therapy employing the present invention device results in enhanced surgical performance. Photodynamic therapy consists essentially of the application of a photosensitive substance, usually be injection into the bloodstream or by local application to the tissue surface. This photosensitizer remains longer and in higher concentrations in tumor tissue than in normal tissue. As is well known to those skilled in the art, different photosentizers are used and under investigation. They are also activated by different wavelengths. Hematoporphyrin or Photophrin, for instance, may be used to treat prostate tumors by 630 nm laser radiation. In this case, the device described in the invention can be particularly useful as it enables the application of a well directed dosage and deep penetration without over exposing the tissue surface due to its large radiation emission area. Thus, a present invention fiber may inserted into a cystoscope which has been inserted into the urethra such that the present invention fiber tip is visible through the cystoscope's image guide. The fiber is twisted so as to achieve the desired lasing direction. A directional marker on the fiber tip or the pilot beam from a low intensity helium neon laser can be typically used for aiming. The main laser beam is fired and the radiation impacts on the tissue to shrink/remove it. Liquid irrigation can be used during the procedure. Again, procedures such as this are well within the purview of the artisan. In order to perform this procedure in a controlled and safe manner, a present invention radial medical delivery device 102 comprising an optical fiber 31, a multilumen channel 32, an inflatable balloon 33 as well as temperature sensing fibers for dosage monitoring such as fibers 34 and 35, is introduced into the urethra 35. Fiber 31 has grooves 41, 42 and 43 and cut end 44, as shown. After inflating the balloon that is transparent to the radiation wavelength used in the procedure (example, 1064 nm) radiation is directed at the prostate 36. The inclinations of the grooves 41, 42 and 43 and cut tip 44, vary in this example, so that the radiation represented incoming by arrows 45, 46, 47 and 48, and outgoing by arrows 51, 52, 53 and 54, converges toward the prostate 36.

The radiation is thus effectively penetrating the urethra wall 38 in a less concentrated form than it is hitting the prostate, thus limiting the damage done to it.

The balloon 33 can be cooled by gas or liquid to further protect the prostate wall. By feeding the temperature reading obtained via sensing fibers 34 and 35 back to a laser power control, an optimum radiation level can be obtained.

Figure 3:
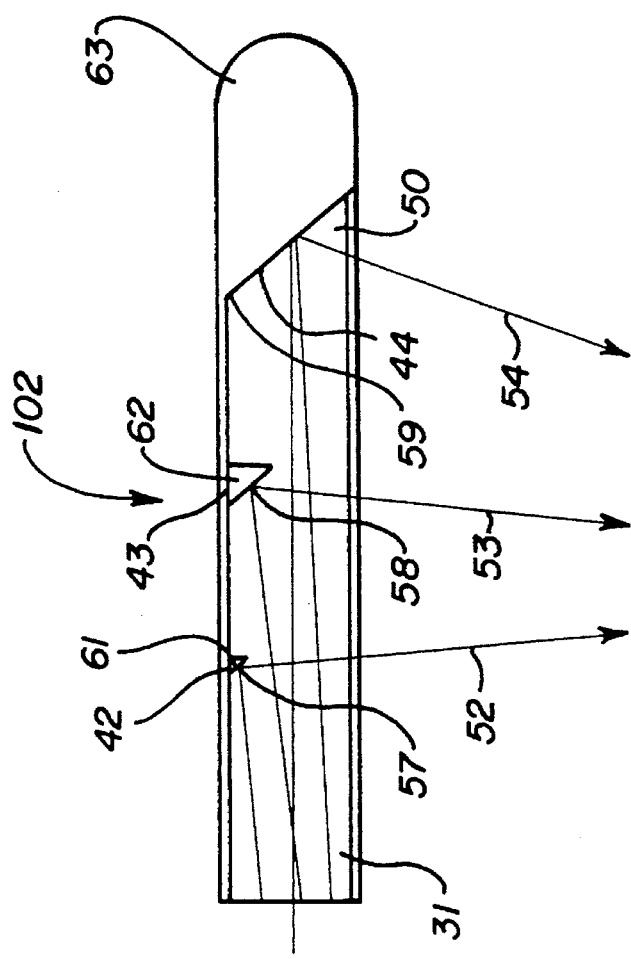
FIG. 3 is a detailed view of FIG. 2 showing reflective metal coating used for deflection.

In this example of a preferred embodiment of the radial medical delivery device, the grooves 41, 42, 43 and the cut tip 44 of the distal end 50 of the fiber, shown in part in FIG. 3 are at least partially covered by a reflective metal 57, 58 and 59 (such as gold) to deflect the radiation. Dark areas 61, 62 and 63, for example, receive substantially no radiation.

Figure 4:
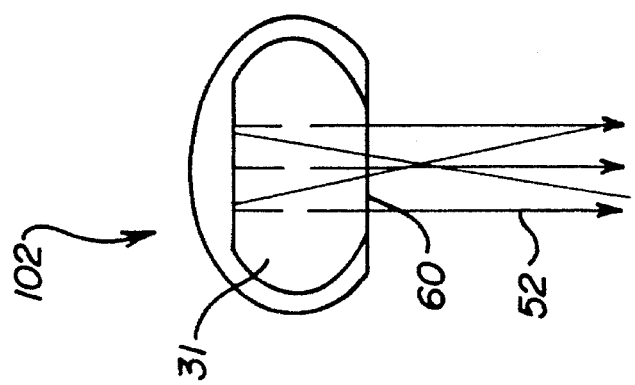
FIG. 4 is a cross section of FIG. 3.

FIG. 4 shows a cross section and illustrates how, by flattening the lower side 60 of the fiber 31 focusing in all but the desired dimension and direction may be avoided.

The superiority over the present state of the art will now be clear: Compared to a single reflective (or totally reflective) point source on the end of a fiber the energy density penetrating through the balloon and the urethra wall is much lower and a certain degree of focusing can be achieved, if desired, towards the prostate.

Figure 5A:
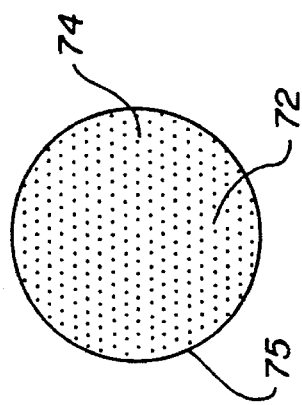
FIGS. 5 and 5a shows a conventional state of the art Photo Dynamic Therapy delivery device.
Figure 5:
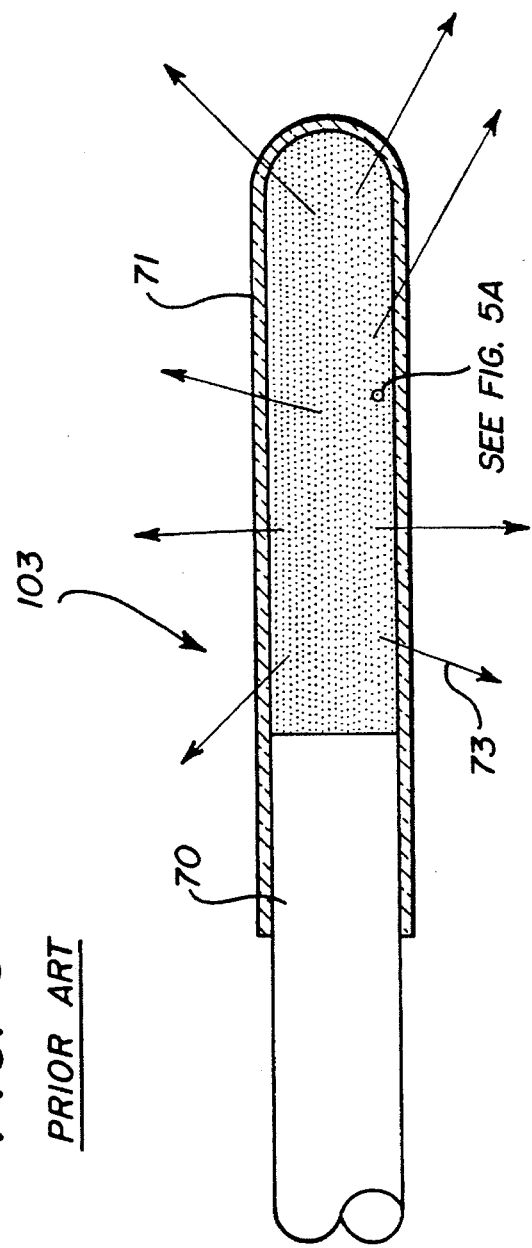

FIG. 5 shows prior art systems 103 with typical scattering cap 71 employing a glue 74 mixed with scattering particles 72. The radiation from fiber 70 scatters randomly and has no predetermined area of application. The present invention device is much better directed, more power can be handled, and more successful surgeries can be accomplished. For example, with the FIG. 5 prior art system 103, radiation in direction 73 might damage the sphincter muscle in a prostate irradiation case. The controlled directed irradiation utilizing the present invention device will avoid such likelihoods.

When the present invention is applied for prostate degeneration, a fiber of synthetic silica could be used to deliver the laser power at 1064 nm. The fiber for sensing the tissue temperature may be of silver halide semi crystalline material (transmitting a wavelength range between 4 um and 16 um). In this case, the cladding on the core may be air.

Any other available or known materials may be used for the fiber for a particular application without exceeding the scope of the present invention. For example, it can be equally possible to make the radial medical radiation delivery device employing a silver halide fiber for the laser delivery itself.

In this case a CO or $CO_2$ laser can be used as a radiation source with wavelength of around 5 um and typically 10.6 um. In this case, the same fiber through which the laser radiation passes for irradiating the tissue can also be used to measure tissue temperature as well, as illustrated in FIG. 6 and FIG. 7.

Figure 6:
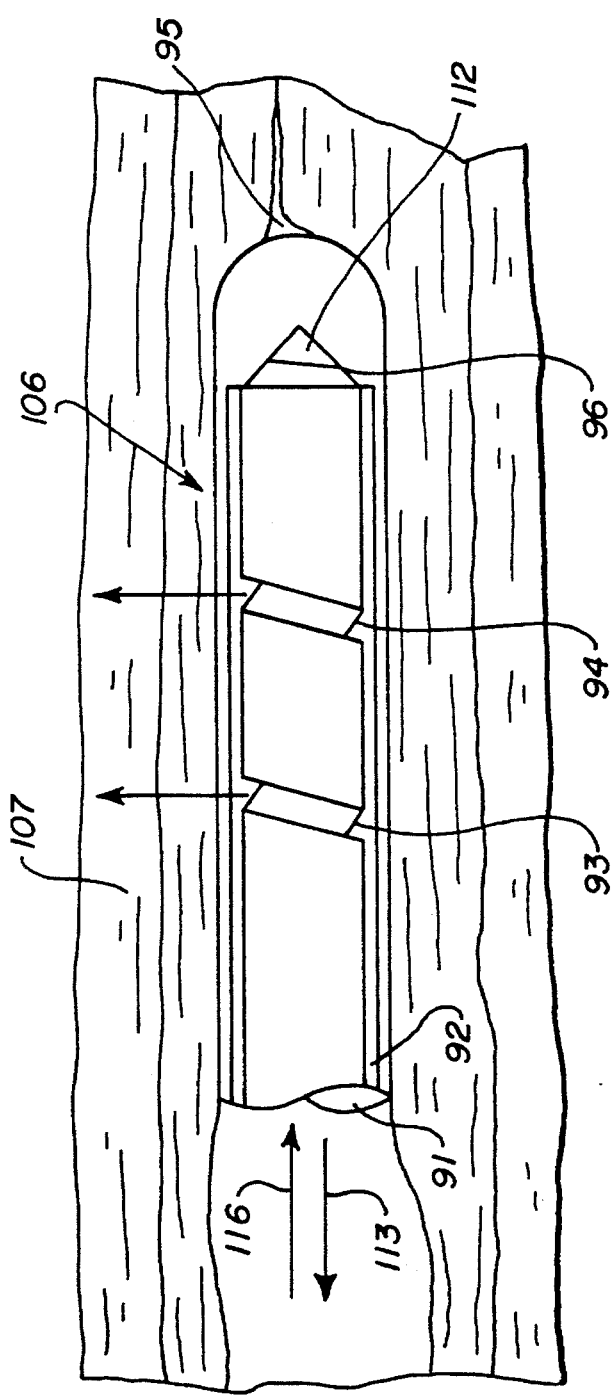
FIG. 6 shows a delivery device with spiral grooves.
Figure 7:
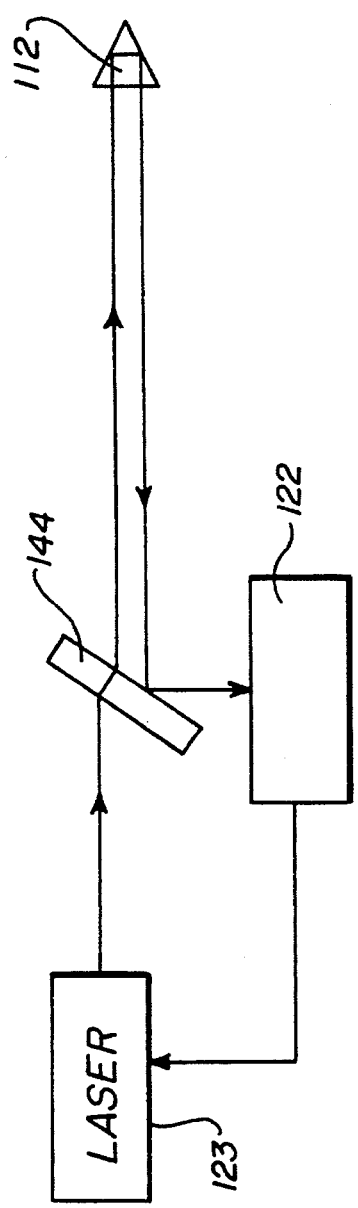
FIG. 7 shows a power control system operated by sensing through the same fiber.

FIG. 6 shows present invention device 106 a silver halide fiber consisting of core 91 and clad 92. In this case, circular cut angled grooves 93 and 94 and tip 96, as well as a transparent cap 95 are included. While the laser radiation 116 is targeted towards the tissue 107, the temperature radiation from tissue 108 is picked up by the fiber and transmitted via a reflector 112 formed at tip 96, in the optical path of the transmission, and fed back as shown by arrow. As shown in FIG. 7, this feedback is diverted via prism 114 towards a laser control module 122 thus controlling the power output of the laser 123 in line with procedural requirements.

It is evident that in some instances it may be preferable from a manufacturing standpoint to fuse a tip of a fiber containing the grooves on to another fiber, thus effectively in the end obtaining a device similar in operative characteristics to the ones described so far, and the present invention device may include a fiber formed of such joined sections without exceeding the scope of the present invention.

Clearly, in some instances it may be advantageous to build the delivery system of more than one delivery fiber processing the characteristic as described so far in this invention, for instance in order to provide higher flexibility of the device while still maintaining a certain total cross section, a fiber bundle may be used, without exceeding the scope of the present invention. Such bundles may have fibers with identical configurations but slightly staggered to enhance transmission, or may form components of a single desired configuration, depending upon the application(s) intended.

Figure 8:
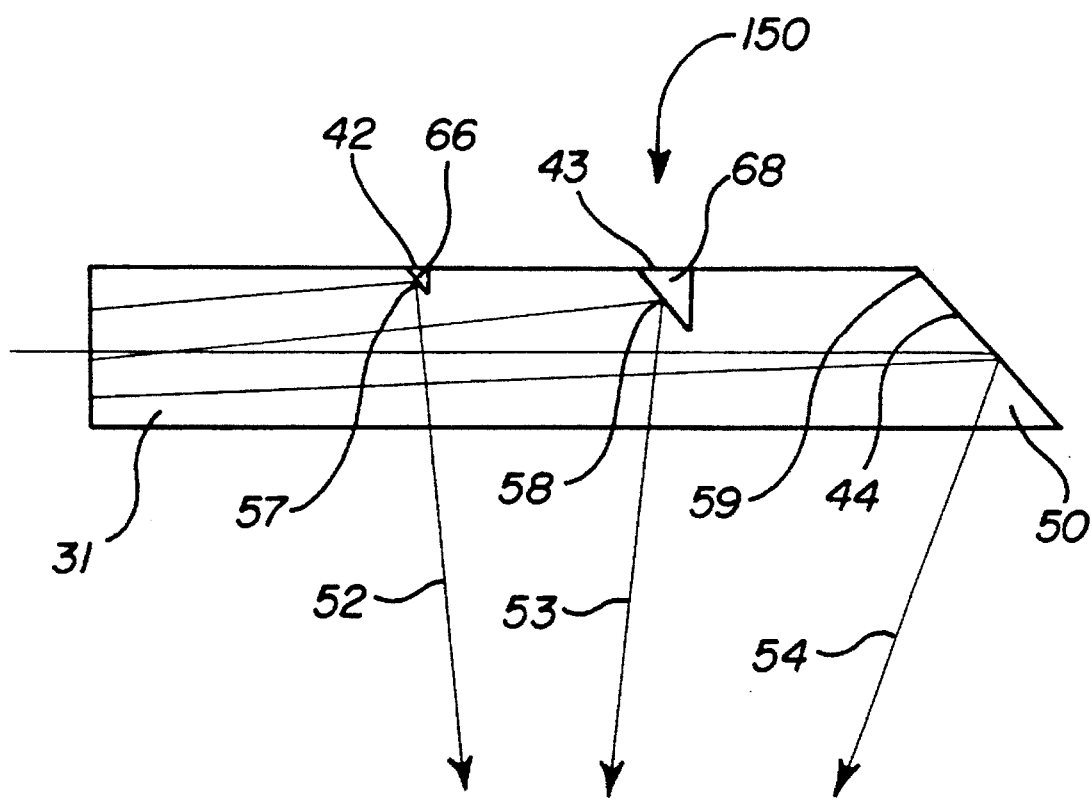
FIG. 8 shows a preferred embodiment without a cap wherein the grooves are filled with a material having a significantly lower reflective index than the fiber core.

FIG. 8 illustrates a side view of present invention device 150, another preferred embodiment of the invention, at its distal end wherein like parts are like numbered to those in FIG. 3. In this embodiment, there is no cap and grooves 42 and 43 are filled with a material 66 and 68 with a significantly lower reflective index than the fiber core. This material may be, for instance, Teflon AF (from DuPont) and the method of its deposition into the grooves is well within the purview of the artisan.

Obviously, numerous modifications and variations of the present invention are possible in light of the above teachings. It is therefore understood that within the scope of the appended claims, the invention may be practiced otherwise than as specifically described herein.

What is claimed is:

1. A medical delivery system capable of emitting radiation with wavelengths between 190 nm and 16 um in one or more essentially directed, predetermined patterns, which comprises:
at least one solid optical fiber, having a core and a cladding on said core and said cladding having a refractive index smaller than the core, having an input end suitably configured to connect to an appropriate radiation source and having a distal end in the proximity of which two or more grooves having been formed in a predetermined pattern are penetrating into the core, said grooves having at least partial reflector capability so as to deflect radiation thereto radially in one or more predetermined patterns.

2. A medical delivery system as claimed in claim 1, further characterized by a cap being placed over said at least one fiber at its distal end and over said two or more grooves, and by the enclosure of gas pockets in the grooves by means of said cap.

3. A radial delivery system as claimed in claim 1, further characterized by filling the grooves with a material having a significantly lower reflective index than the fiber core.

4. A medical radiation delivery system as claimed in claim 1, wherein the grooves have a reflective coating on at least one side.

5. A medical radiation delivery system as claimed in claim 1, wherein said at least one fiber is a quartz glass or synthetic silica fiber and the radiation transmitted is between 190 and 3000 nm.

6. A medical radiation delivery system as claimed in claim 1, wherein the fiber is a silver halide fiber and the radiation transmitted is between 4 um and 16 um.

7. A medical radiation delivery system as claimed in claim 1, wherein the grooves are only on one side of the device.

8. A medical radiation delivery system as claimed in claim 1, wherein the grooves have inclinations which vary in the optical fiber so as to give a radiation pattern converging at a predetermined distance from the fiber axis.

9. A medical radiation delivery system as claimed in claim 1, which further includes means for collecting radiation form the irradiated surface, and memos for controlling the energy level delivered responsive to collected radiation.

10. A system according to claim 9 wherein said means for collecting includes means for returning said radiation along said at least one optical fiber to a laser control device.

11. A system according to claim 9 wherein said means for collecting includes at one temperature sensing fiber extending beyond said cladding for exposure to a temperature at a vicinity of a treatment site for transmitting a temperature signal to a laser control device.

12. A medical radiation delivery device system as claimed in claim 1, further comprising:

an inflatable balloon coveting an end of said at least one solid optical fiber;

at least one temperature control sensors in said inflatable balloon;

said inflatable baboon being transparent at least over a cylindrical portion to the radiation wavelength used and incorporating said at least one solid optical fiber inside said inflatable balloon.

13. A medical radiation delivery device system as claimed in claim 12, wherein; said at least one optical fiber is in a multilumen channel within said inflatable balloon and extends beyond said multilumen channel in a movable manner.

14. A medical radiation delivery device system as claimed in claim 1, further comprising:

an inflatable baboon covering an end of said at least one optical fiber;

dosage monitoring fibers affixed to said inflatable baboon transparent at least over an essential part of its surface to the radiation wavelength used.

15. A method of performing a laser prostatectomy procedure, comprising:

(a) the inserting of a cystoscope into the urethra;

(b) positioning a device which includes at least one solid optical fiber, having a core and a cladding on said core and said cladding having a refractive index smaller than the core, having an input end suitably configured to connect to an appropriate radiation source and having a distal end in the proximity of which two or more grooves having been formed in a predetermined pattern are penetrating into the core, said grooves having at least partial reflector capability so as to deflect radiation thereto radially in one or more predetermined patterns; and, (c) irradiating the prostate area to be degenerated.

16. The method of claim 15 wherein said device is further characterized by a cap being placed over said at least one fiber at its distal end and over said two or more grooves, and by the enclosure of gas pockets in the grooves by means of said cap.

17. The method of claim 16 wherein said device is further characterized by filling the grooves with a material having a significantly lower reflective index than the fiber core.

18. A method of performing a prostate degeneration procedure comprising:

(a) inserting at least the distal end of a device into the urethra, which includes at least one solid optical fiber, having a core and a cladding on said core and said cladding having a refractive index smaller than the core, having an input end suitably configured to connect to an appropriate radiation source and having a distal end in the proximity of which two or more grooves having been formed in a predetermined pattern are penetrating into the core, said grooves having at least partial reflector capability so as to deflect radiation thereto radially in one or more predetermined patterns, and which further includes one or more temperature control sensors affixed on to an inflatable balloon transparent at least over its cylindrical portion to the radiation wavelength used and incorporating the radiation delivery fiber in the inside of said inflatable balloon;

(b) positioning it as necessary;

(c) inflating the balloon; and, (d) irradiating the prostate area to be degenerated.

19. The method of claim 18, wherein said fiber is located within said inflatable balloon in a movable manner.

20. Method of performing photodynamic therapy, comprising:

(a) applying a photosensitive substance to an area to be treated or to a distal end of the device set forth below;

(b) inserting a device which includes at least one solid optical fiber, having a core and a cladding on said core and said cladding having a refractive index smaller than the core, having an input end suitably configured to connect to an appropriate radiation source and having a distal end in the proximity of which two or more grooves having been formed in a predetermined pattern are penetrating into the core, said grooves having at least partial reflector capability so as to deflect radiation thereto radially in one or more predetermined patterns; and, (c) irradiating the tissue to an intended dosage level.

21. The method of claim 20, further characterized by a cap being placed over said at least one fiber at its distal end and over said two or more grooves, and by the enclosure of gas pockets in the grooves by means of said cap.

22. The method of claim 20, further characterized by filling the grooves with a material having a significantly lower reflective index than the fiber core.

* * * * *